United States Patent
Higgins et al.

(10) Patent No.: US 11,541,224 B2
(45) Date of Patent: Jan. 3, 2023

(54) INTRAVASCULAR PUMP WITHOUT INDUCER AND CENTRIFUGAL FORCE-DRIVEN EXPANSION OF IMPELLER BLADES AND/OR EXPANDABLE AND COLLAPSIBLE IMPELLER HOUSING

(71) Applicant: Cardiovascular Systems, Inc., St. Paul, MN (US)

(72) Inventors: Joseph P. Higgins, Minnetonka, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 264 days.

(21) Appl. No.: 16/524,554

(22) Filed: Jul. 29, 2019

(65) Prior Publication Data
US 2020/0030507 A1    Jan. 30, 2020

Related U.S. Application Data

(60) Provisional application No. 62/711,740, filed on Jul. 30, 2018.

(51) Int. Cl.
*A61M 60/00*    (2021.01)
*A61M 60/10*    (2021.01)
(Continued)

(52) U.S. Cl.
CPC .......... *A61M 60/148* (2021.01); *A61M 60/13* (2021.01); *A61M 60/216* (2021.01);
(Continued)

(58) Field of Classification Search
CPC .............. A61M 60/205; A61M 60/148; A61M 60/135; A61M 60/414; A61M 2205/3334; A61M 1/00; A61M 1/80; A61M 60/00; A61M 60/10; A61M 60/122; A61M 60/126; A61M 60/165; A61M 60/13;
(Continued)

(56) References Cited

U.S. PATENT DOCUMENTS

| 2008/0103591 A1 | 5/2008 | Siess |
| 2008/0132747 A1 | 6/2008 | Shifflette |

(Continued)

FOREIGN PATENT DOCUMENTS

| EP | 2692369 A1 | 2/2014 |
| WO | 2003/103745 A2 | 12/2003 |

(Continued)

OTHER PUBLICATIONS

International Search Report and Written Opinion, dated Nov. 15, 2019, for PCT Application No. PCT/US19/44053, filed Jul. 30, 2019.

(Continued)

*Primary Examiner* — Jon Eric C Morales
(74) *Attorney, Agent, or Firm* — Barnes & Thornburg LLP; Jeffrey R. Stone

(57) ABSTRACT

The present invention provides an intravascular blood pump comprising an impeller housing and/or impeller blade(s) that may be expandable and collapsible. The blade(s) and/or impeller housing may be biased to expand or may be (Continued)

expanded by centrifugal forces generated during rotation of the impeller and blades with an operatively connected rotational motor.

28 Claims, 6 Drawing Sheets

(51) Int. Cl.
| | |
|---|---|
| *A61M 60/148* | (2021.01) |
| *A61M 60/554* | (2021.01) |
| *A61M 60/808* | (2021.01) |
| *A61M 60/546* | (2021.01) |
| *A61M 60/13* | (2021.01) |
| *A61M 60/216* | (2021.01) |
| *A61M 60/411* | (2021.01) |

(52) U.S. Cl.
CPC ........ *A61M 60/411* (2021.01); *A61M 60/546* (2021.01); *A61M 60/554* (2021.01); *A61M 60/808* (2021.01); *A61M 2205/3365* (2013.01)

(58) Field of Classification Search
CPC .............. A61M 60/152; A61M 60/157; A61M 60/161; A61M 60/20; A61M 60/247; A61M 60/216; A61M 60/221; A61M 60/226; A61M 60/232; A61M 60/237; A61M 60/242; F04D 29/181
See application file for complete search history.

(56) References Cited

U.S. PATENT DOCUMENTS

| | | |
|---|---|---|
| 2016/0263298 A1 | 9/2016 | Er |
| 2016/0271309 A1 | 9/2016 | Throckmorton et al. |
| 2018/0169313 A1 | 6/2018 | Schwammenthal et al. |

FOREIGN PATENT DOCUMENTS

| | | |
|---|---|---|
| WO | 2011/076349 A1 | 6/2011 |
| WO | 2011/076439 A1 | 6/2011 |

OTHER PUBLICATIONS

Extended European Search Report dated Mar. 21, 2022, issued in EP Application No. 19845091.8.

INTRAVASCULAR PUMP WITHOUT INDUCER AND CENTRIFUGAL FORCE-DRIVEN EXPANSION OF IMPELLER BLADES AND/OR EXPANDABLE AND COLLAPSIBLE IMPELLER HOUSING

CROSS-REFERENCE TO RELATED APPLICATIONS

This application claims priority to U.S. Provisional Patent Application No. 62/711,740, filed Jul. 30, 2018 and titled INTRAVASCULAR PUMP WITH CENTRIFUGAL FORCE-DRIVEN EXPANSION, the contents of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular blood pump with an expandable and collapsible inlet region.

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a flow inducer, known in the art as component that directs flow into the impeller from the inflow apertures or inlet; a rotational impeller; and a flow diffuser and/or outflow structure known in the art as functioning to straighten or redirecting the rotational flow created by the rotational impeller into axial flow; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the flow inducer 6 before being urged forward by the rotating impeller 8. The blood flow may then be modified by a flow diffuser 9 and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a stationary inducer or flow straightener encountered by blood upon entry into the pump which can contribute to, inter alia, thrombosis and/or hemolysis. Fourth, reducing crossing profile of the VAD or LVAD device is critical for reasons discussed herein, a design requirement made more difficult by the need to extend electric leads across or along the housing of the device, wherein the electrical leads may be used for, e.g., powering and/or communicating with a motor or sensor(s) or other operational powered element. In this connection, electric leads require profile reduction to keep the crossing profile as low as possible, as well as insulation and/or spacing between adjacent leads where such insulation and/or spacing is necessary or desired.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 3:
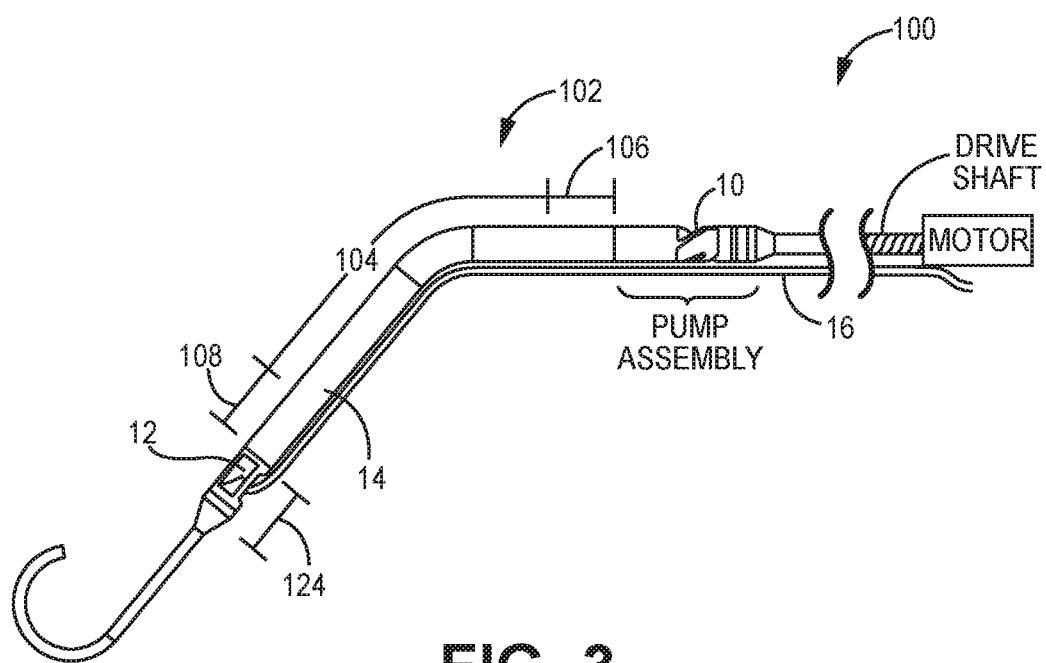
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller or rotor 8 or pump assembly. However, as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200.

With reference generally to the Figures, device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, the housing H of device 100 in FIG. 3 may be non-expandable.

Figure 4:
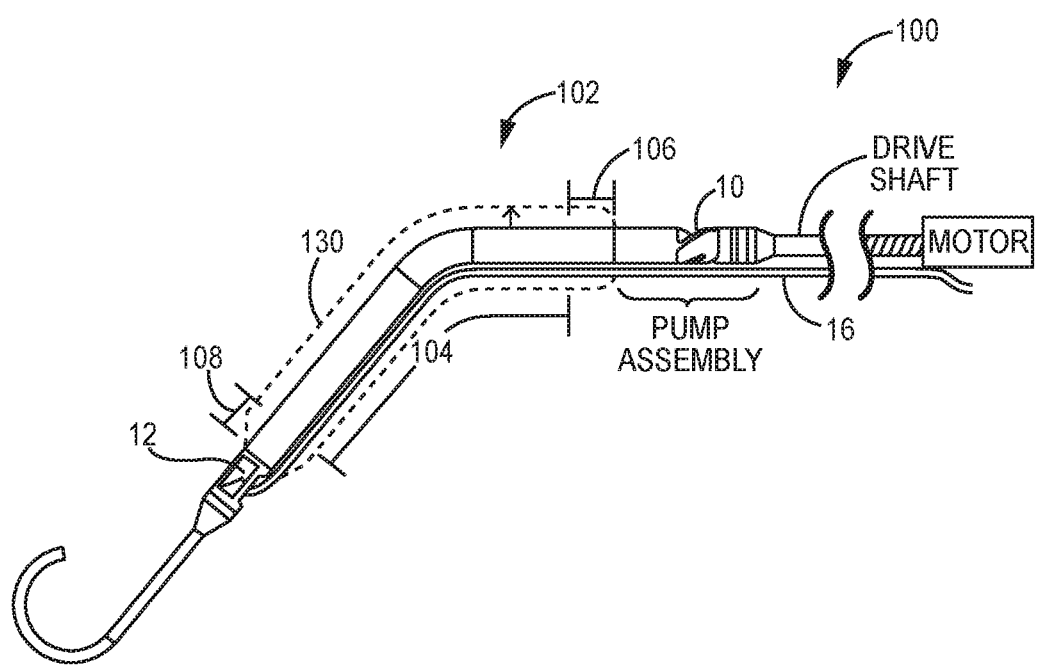
FIG. 4 is a side cutaway view of one embodiment of the present invention.

FIG. 4 illustrates an expandable embodiment of device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 may comprise an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold. In other cases, at least a portion of the expandable region 102, e.g., a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor. Further, as discussed above, device 100 may comprise an expandable housing H or region 102 or may be non-expandable.

In many of the embodiments described herein, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

The expandable region 102 described herein is merely exemplary and not limiting in any regard. As such, any expandable housing H of a blood pump device 100 is readily adaptable to the various embodiments of the present invention relating to insulation and/or spacing and/or profile reduction or integration of electrical leads or conductors E within or along the blood pump housing. Expandable region 102 may also comprise a single region capable of expansion and collapse.

Figure 5:
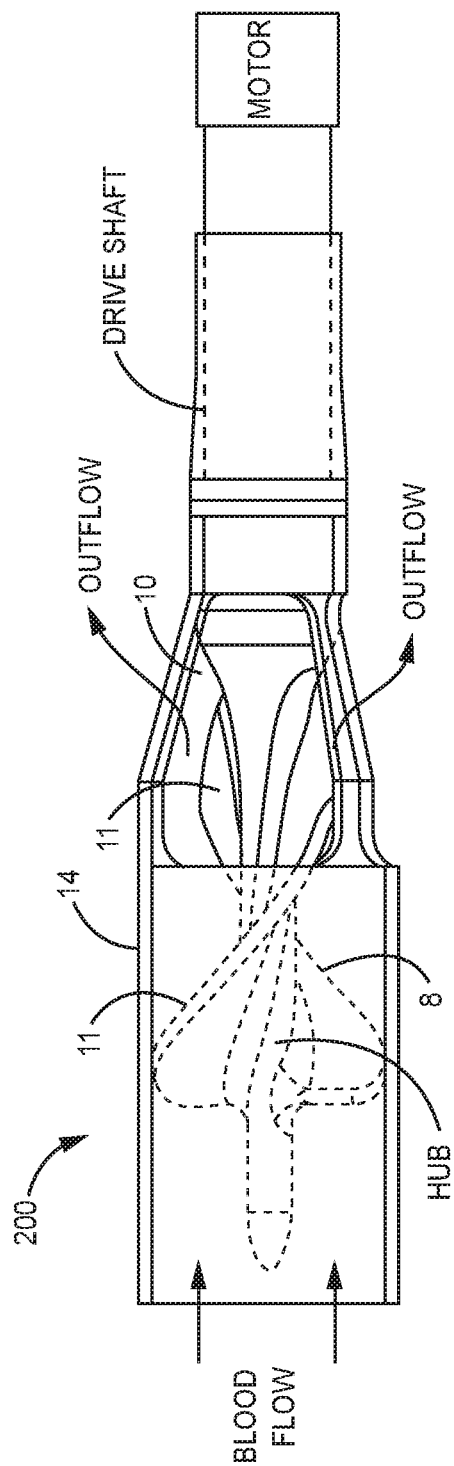
FIG. 5 is a side cutaway of one embodiment of the present invention.

Turning now to FIG. 5, an exemplary pump assembly or impeller assembly 200 is illustrated.

Figure 1:
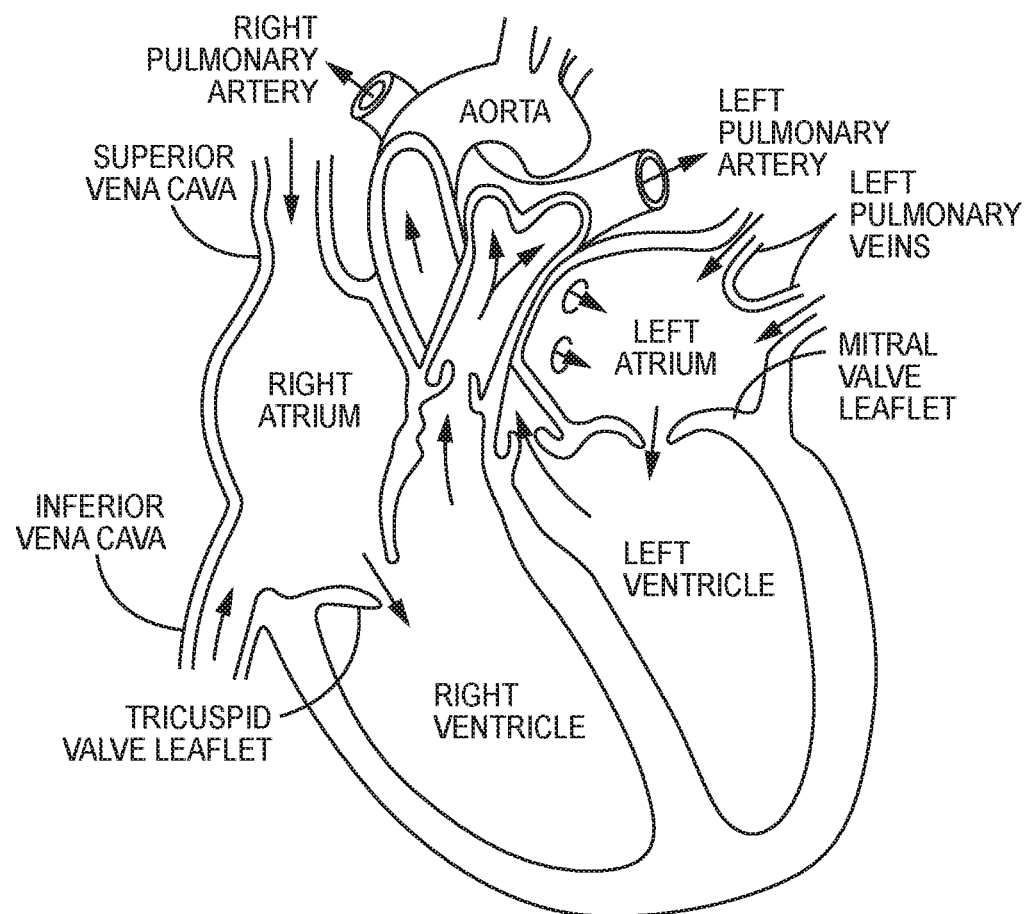
FIG. 1 is a cutaway view of the human heart.
Figure 2:
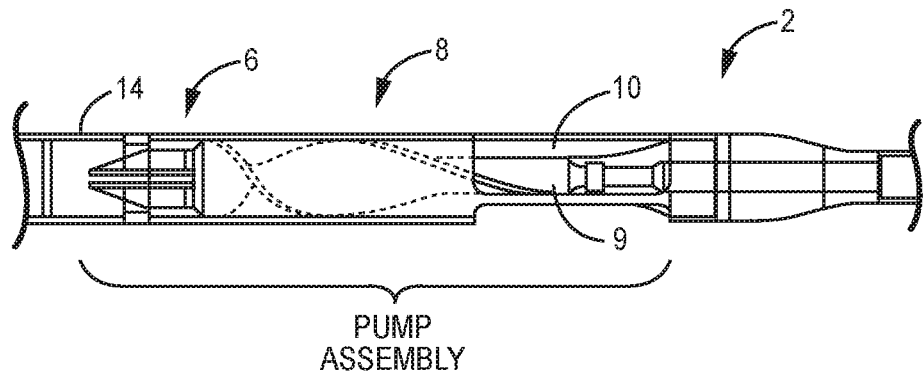
FIG. 2 is a cross-sectional view of a prior art device.

Initially, in contrast to the known impeller assembly shown in FIG. 2 which comprises a flow inducer 6 and flow diffuser 9, the exemplary pump or impeller assembly of FIG. 5 completely eliminates the flow inducer 6 and the flow diffuser 9 of the impeller assembly found in known pumps. Applicant has found that the inducer 6 and/or diffuser 9 are not needed for effective control or manipulation of the incoming blood flow and that the additional stationary surface area and interconnections between at least the inducer 6 and the distal end of the rotating impeller 8 provide increased risk of thrombosis. Thus, the blood is induced to flow through the cannula of by actuating the pump or impeller assembly to rotate at a predetermined speed, without aid or requirement of a flow inducer. The blood thus flows directly to the rotating impeller 8 comprising blades 11 and is urged out of the cannula or lumen of the device at outlet apertures 10 by the rotating impeller blades 11, without aid or requirement of a flow diffuser or straightener.

Figure 6A:
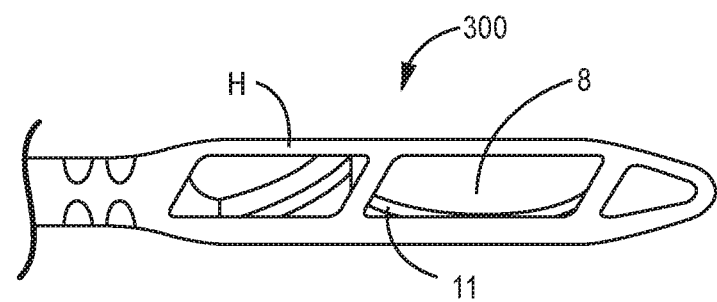
FIG. 6A is a side cutaway of one embodiment of the present invention.
Figure 6B:
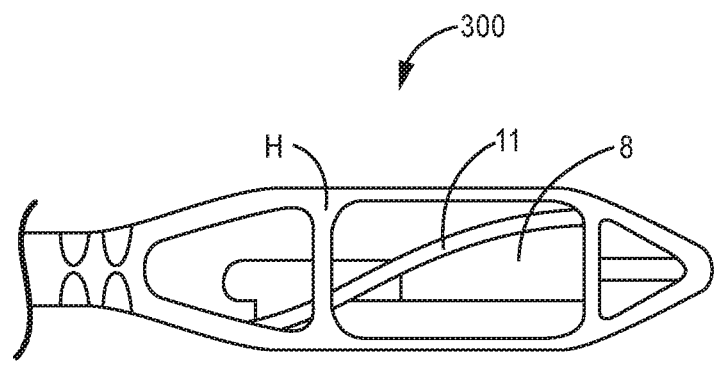
FIG. 6B is a side cutaway of one embodiment of the present invention.

Turning now to FIGS. 6A and 6B, another embodiment of the blood pump device 300 comprises a centrifugal-force driven expansion mechanism as shown. FIG. 6A illustrates a collapsed, delivery configuration while FIG. 6B shows pump assembly region in an expanded, working configuration.

Thus, the impeller housing H may comprise an expandable stent-frame as is known in the art and discussed supra. The impeller housing H may therefore move between a collapsed, delivery configuration to an expanded, working configuration during delivery and retraction. The device 300 may be delivered through a sheath (not shown but as is well known in the art) which forces the impeller housing H into the collapsed, delivery/retracted configuration of FIG. 6A. When the device 300 is extended outside the distal end of the lumen of the delivery sheath, the impeller housing H, which may be biased to expand and, when released from the constrictions of the delivery sheath lumen may expand to achieve the expanded working configuration of FIG. 6B. The impeller housing H may be moved back to the collapsed delivery configuration by retracting the device housing back into the delivery sheath lumen.

With reference to FIGS. 5 and 6A-6B, the blades 11 may comprise at least one blade 11 and the at least one blade may comprise a helical shape as illustrated. Each of the at least one helical blades 11 may comprise a first side and a second opposing side.

In combination with the collapsible and expandable impeller housing H configuration, the blades attached to the impeller are also enabled to move between a collapsed configuration and an expanded working configuration to further reduce the outer diameter of the impeller housing H with associated impeller 8 and blades 11 during delivery and retraction.

Again with reference to FIGS. 5A and 6A-6B, the first side of the at least one helical blade 11 may be configured to collapse against the outer surface of the hub to achieve a retracted configuration. The first side of the at least one helical blade may expand away from the outer surface of the hub to achieve an expanded configuration.

Accordingly, the retracted blades of FIG. 6A may open solely by rotating the impeller at a speed sufficient to generate a centrifugal force on the blade(s) 11 to cause the blade(s) 11 to move from retracted to extended or expanded as in FIG. 6B. While fluid flow forces may assist with this transition, the blade(s) 11 may be configured such that they will expand by centrifugal force alone, i.e., the blade(s) 11 will, in this embodiment, expand or extend to working configuration in a vacuum and without need or aid of fluid forces to assist in the expansion.

The exemplary impeller housing 11 may, by these mechanisms, be transitioned between an exemplary range of 14 fr to 9 fr.

Accordingly, as described above, the impeller housing 11 may be self-expanding, e.g., a stent-like frame or other memory shape material. The blade(s) 11 may be adapted to lock into an extended or expanded position when open/expanded, thus requiring a force to overcome the locking force when the blade(s) 11 are to be collapsed. In other embodiments, the blade(s) 11 may comprise a biased retracted position or a biased extended position.

In the embodiment shown, retraction of the blade(s) 11 may occur at the same time and in essentially the same way as retraction of the impeller housing H, by retracting the impeller housing H and related assembly comprising the housing H, impeller 8 and blade(s) 11 distally into the delivery sheath lumen, thus forcing the housing H to collapse as well as the blade(s) 11 to collapse against the impeller hub (see FIG. 5) to achieve the collapsed delivery/retraction configuration.

In some embodiments the impeller housing H may be expanded and/or collapsed as a result of rotation of the drive shaft and resulting rotation of the impeller blades 11 which create an outward force that pushes radially outwardly on the impeller housing H, moving it from a collapsed configuration to an expanded configuration. At the expanded point, the impeller housing H may be held at expanded configuration using a locking mechanism or be held in the expanded configuration as a result of the generated radially outward fluid forces resulting from the blade(s) 11 rotation.

In some embodiments, the impeller may first be pulled distally into a proximal retraction zone or retraction cone of the impeller housing H, with the modified assembly then pushed or retracted distally into the lumen of the delivery sheath where the impeller housing H and impeller blade(s) 11 retract to the collapsed configuration.

In other embodiments, reversing rotation of the impeller 8 may serve to move the extended/expanded blade(s) 11 to a collapsed position or, in some embodiments unlocking the locked extended blade(s) 11 so that retraction of the expanded blade(s) 11 into the delivery sheath will enable completion of the collapsing of the blade(s) 11.

In some cases, the blade(s) 11 may be biased to collapse and a threshold impeller 8 rotational speed is required to generate centrifugal force sufficient to overcome the biased collapsing of the blade(s) 11 to reach the expanded working configuration. The slowing of the rotational speed of the impeller 8 below the expansion/collapse threshold will thus allow the blade(s) 11 to collapse against the impeller hub.

Moreover, the combination of a biased collapsing force on the blade(s) 11 with the variable rotational speed of the impeller 8 may be used to modify the pitch of the blades (11) along the impeller 11, e.g., the angle of the blade(s) 11 in relation to the impeller hub, during operation. A minimum threshold expansion rotational speed may be required to begin to extend the blade(s) 11 while a higher rotational speed may be required to fully extend the blade(s) 11. Any rotational speed between the minimum threshold expansion rotational speed and the fully extended rotational speed may therefore be employed to generate a blade pitch relative to the impeller hub of effectively infinite possible magnitudes and that may allow the operator to use the resulting variable blade pitch and rotational speed combinations to more effectively achieve the targeted blood flow rate and/or pressures.

Figure 7:
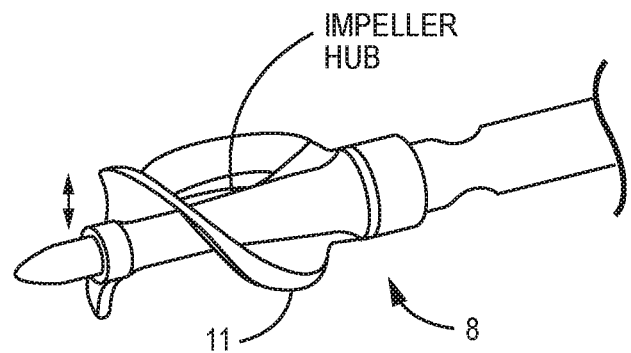
FIG. 7 is a cutaway perspective view of one embodiment of the present invention.
Figure 8:
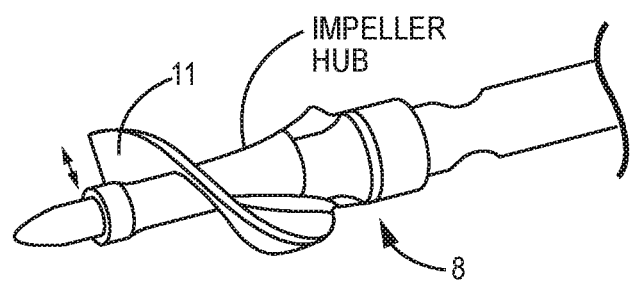
FIG. 8 is a cutaway perspective view of one embodiment of the present invention.
Figure 9:
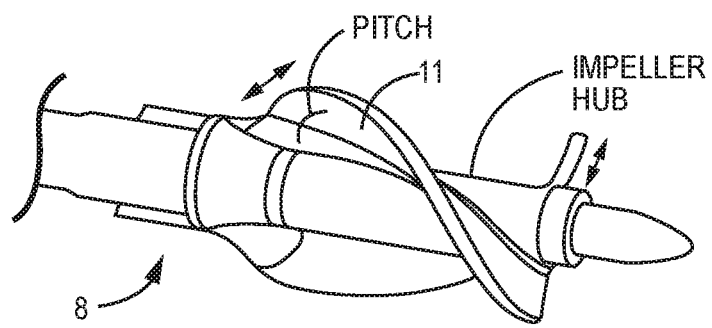
FIG. 9 is a cutaway perspective view of one embodiment of the present invention.

FIGS. 7-9 below provide additional disclosure of impeller 8 embodiments comprising expandable blade(s) 11 that may be expanded out of, or collapsed at least partially into, the impeller hub by the mechanisms discussed above. The impeller housing H is not shown in FIGS. 7-9, but these embodiments will function according to the preceding disclosure including but not limited to the impeller housing H.

In all cases described herein, the rotational speed of the impeller 8, when above the minimum threshold expansion rotational speed, is proportional to the degree of expansion achieved by the blade(s) 11 up to the rotational speed where expansion is complete and total where the blade(s) 11 may "lock" into expanded position or may freely move in/out of the impeller hub according to rotational speed as discussed herein. Thus, the expansion degree may be modified by adjusting rotational speed of the impeller 8, when the rotational speed is between the minimum threshold expansion rotational speed and the total expanded rotational speed.

Further, as discussed herein, the expansion and contraction of the impeller housing H may be done with, or without, the blade(s) 11 expansion and retraction. If done without the blade(s) 11 retraction and expansion embodiment, then the impeller housing H in its collapsed configuration will be limited to the radially measured diameter of the blade(s) 11. If done with the retraction and expansion blade(s) 11 embodiments, then it is possible that the collapsible diameter is limited by the radial diameter of the impeller hub.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump assembly comprising a motor in operative rotational engagement with an impeller assembly, the impeller assembly comprising an impeller housing, an impeller within the impeller housing, the impeller comprising an impeller hub having an outer surface and at least one helical blade in operative engagement with the impeller hub,
    wherein the at least one helical blade comprises a first side and a second side opposing the first side, wherein the first side of the at least one helical blade is configured to retract against the outer surface of the impeller hub to achieve a retracted position, and wherein the first side of the at least one helical blade is configured to expand away from the outer surface of the impeller hub to achieve any one of a plurality of expanded positions,
    wherein the at least one helical blade is not biased to expand away from the impeller hub in order to achieve any one of the plurality of expanded positions,
    such that the at least one helical blade is configured to expand away from the impeller hub and the retracted position to achieve any expanded position in the plurality of expanded positions only as a result of centrifugal forces generated during rotation of the impeller.

2. The blood pump assembly of claim 1, wherein the expanded position is a result of the rotational speed of the impeller exceeding a threshold rotational speed.

3. The blood pump assembly of claim 1, wherein the expanded position achieved within the plurality of expanded positions of the at least one helical blade is dependent upon the rotational speed of the impeller and the related generated centrifugal forces.

4. The blood pump assembly of claim 1, wherein the at least one helical blade is biased to retract.

5. The blood pump assembly of claim 1, further comprising the impeller housing adapted to collapse and expand.

6. The blood pump assembly of claim 5, wherein the impeller housing comprises a stent frame.

7. The blood pump assembly of claim 5, wherein the impeller housing is biased to expand.

8. The blood pump assembly of claim 5, wherein the impeller housing expands as a result of outwardly radially directed fluid forces generated during rotation of the impeller.

9. The blood pump assembly of claim 1, further comprising the impeller housing adapted to collapse and expand.

10. The blood pump assembly of claim 9, wherein the impeller housing comprises a stent frame.

11. The blood pump assembly of claim 9, wherein the impeller housing is biased to expand.

12. The blood pump housing of claim 9 wherein the impeller housing expands as a result of outwardly radially directed fluid forces generated during rotation of the impeller.

13. A blood pump assembly comprising:
a blood pump comprising an impeller housing and an impeller operatively disposed at within the housing, and at least one helical blade, the at least one helical blade comprising a first side and a second side opposing the first side and operatively attached to the impeller at an impeller hub, the impeller hub comprising an outer surface,
wherein the impeller housing and the at least one helical blade are each adapted to move between a collapsed or retracted position against the outer surface of the impeller hub, wherein the first side of the at least one helical blade collapses against the outer surface of the impeller hub in the collapsed position and at least one expanded position in a plurality of expanded positions, wherein the first side of the at least one helical blade expands away from the outer surface of the impeller hub,
wherein the at least one helical blade is biased to collapse into the collapsed or retracted position against the impeller hub and is not biased to expand away from the retracted position against the impeller hub into any one of the plurality of expanded positions, and
wherein the expansion of the at least one helical blade away from the retracted position to any expanded position in the plurality of expanded positions is achieved only by rotating the impeller with an operatively connected motor at a rotational speed sufficient to generate centrifugal force with a magnitude that will cause the at least one helical blade to expand from the retracted position.

14. The blood pump assembly of claim 13, wherein the expansion of the impeller housing from the retracted position is achieved by generating outwardly directed fluid forces during rotation of the impeller and at least one helical blade.

15. The blood pump assembly of claim 13 wherein the impeller housing is biased to expand.

16. The blood pump assembly of claim 13, wherein the impeller housing comprises a stent-like frame.

17. The blood pump assembly of claim 13, wherein an initial and at least partial collapsing of the expanded at least one helical blade is achieved by reversing the rotation of the impeller.

18. The blood pump assembly of claim 13, wherein the at least one helical blade in an expanded position is at least partially collapsed by slowing the impeller rotational speed below a threshold rotational speed.

19. The blood pump assembly of claim 18, wherein the at least one helical blade comprises a pitch angle relative to the impeller hub when in the expanded position and a different pitch angle when in the at least partially collapsed position.

20. The blood pump assembly of claim 19, wherein the pitch angle of the at least one helical blade is variably dependent on the rotational speed.

21. The blood pump assembly of claim 20, wherein the blood flow rate and/or pressure resulting from rotation of the impeller is configured to be varied and optimized based on the pitch angle of the at least one helical blade that that is variably dependent on the rotational speed.

22. A blood pump assembly comprising:
a blood pump comprising an impeller housing and an impeller operatively disposed at within the housing, and at least one helical blade comprising a first side and a second side opposing the first side and operatively attached to the impeller at an impeller hub, the impeller hub comprising an outer surface,
wherein the impeller housing and the at least one helical blade are each adapted to move between a collapsed or retracted position against the impeller hub, wherein the first side of the at least one helical blade collapses against the outer surface of the impeller hub, and at least one expanded position in a plurality of expanded positions, wherein the first side of the at least one helical blade expands away from the outer surface of the impeller hub,
wherein the at least one helical blade is not biased to expand away from the retracted position against the outer surface of the impeller hub into any expanded position in the plurality of expanded positions and
wherein the expansion of the at least one helical blade away from the outer surface of the impeller hub and retracted position to the expanded configuration is achieved only by rotating the impeller with an operatively connected motor at a rotational speed sufficient to generate centrifugal force with a magnitude that will cause the at least one helical blade to expand from the retracted position, and
wherein the expansion of the impeller housing from the retracted position against the impeller hub is achieved by generating outwardly directed fluid forces during rotation of the impeller and at least one helical blade.

23. The blood pump assembly of claim 22 wherein the impeller housing is biased to expand.

24. The blood pump assembly of claim 22, wherein an initial and at least partial collapsing of the expanded at least one helical blade is achieved by reversing the rotation of the impeller.

25. The blood pump assembly of claim 22, wherein the at least one helical blade in an expanded position is at least partially collapsed by slowing the impeller rotational speed below a threshold rotational speed.

26. The blood pump assembly of claim 25, wherein the at least one helical blade comprises a pitch angle relative to the impeller hub when in the expanded position and a different pitch angle when in the at least partially collapsed position.

27. The blood pump assembly of claim 26, wherein the pitch angle of the at least one helical blade is variably dependent on the rotational speed.

28. The blood pump assembly of claim 27, wherein the blood flow rate and/or pressure resulting from rotation of the impeller is configured to be varied and optimized based on the pitch angle of the at least one helical blade that is variably dependent on the rotational speed.

* * * * *